United States Patent [19]
Hager et al.

[11] 3,948,887
[45] Apr. 6, 1976

[54] FLUORINE AND SULFUR-CONTAINING COMPOSITIONS

[75] Inventors: Robert Bonner Hager, Collegeville; Sameeh Said Toukan, Phoenixville, both of Pa.

[73] Assignee: Pennwalt Corporation, Philadelphia, Pa.

[22] Filed: Apr. 8, 1974

[21] Appl. No.: 459,258

Related U.S. Application Data

[62] Division of Ser. No. 283,886, Aug. 25, 1972, abandoned.

[52] U.S. Cl. 260/239 E; 260/77.5 MA; 260/455 A; 260/482 C
[51] Int. Cl.² .................................... C07D 203/00
[58] Field of Search .................... 260/239 E

[56] References Cited
UNITED STATES PATENTS 3,632,571  1/1972  Ray-Chaudhuri .............. 260/239 E
3,721,700  3/1973  Schnierer et al. .............. 260/239 E

*Primary Examiner*—M. J. Welsh

[57] ABSTRACT

The invention concerns epoxides and alcohols of the structures

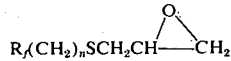

and

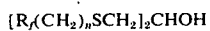

and various derivatives thereof useful in leather and textile treatment.

5 Claims, No Drawings

FLUORINE AND SULFUR-CONTAINING COMPOSITIONS

This is a division of application Ser. No. 283,886, filed Aug. 25, 1972, and now abandoned.

This invention relates to new and useful fluorocarbon compositions, and more particularly to compounds containing sulfur and fluoroalkyl groups. A preferred class of compounds embodied in this invention are fluorocarbon compositions providing oil and water repellency to various substrates which is of a higher degree or is more durable to abrasion than was heretofore possible.

The compositions of this invention are epoxides of the structure

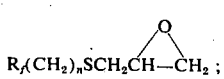

twin-tailed alcohols of the structure $[R_f(CH_2)_nSCH_2]_2CHOH$;

and urethane resins, phosphates and other derivatives and reaction products derived therefrom, where $n$ is an integer of 1–12 and where $R_f$ is a monovalent fluorinated aliphatic radical containing 3 to 15 carbon atoms having perfluoromethyl terminal groups (that portion most distant from the valence bond) and other than carbon atoms in the skeletal chain only oxygen atoms bonded to carbon atoms, the remaining elements of the radical being carbon atoms and fluorine atoms, the skeletal structure of such fluoroaliphatic radical being straight chained or branch chained. Representative $R_f$ groups are $CF_3(CF_2)_y-$, $(CF_3)_2CF(CF_2)_y-$, and $(CF_3)_2CFO(CF_2)_y-$ where $y$ is an integer ranging from 1 to 14.

The compositions of this invention are derived from a known fluorinated mercaptan as the basic building block, having the structure $R_f(CH_2)_nSH$, previously described by Hauptschein et al., U.S. Pat. No. 3,544,663, N.O. Brace, U.S. Pat. No. 3,172,910, and W.S. Friedlander, U.S. Pat. No. 3,088,849. The preparation of the novel compositions of this invention from said mercaptan, as well as a full description of their properties and the scope of the invention is presented below:

PREPARATION OF FLUOROALKYL SULFUR-CONTAINING EPOXIDE.

The fluorine and sulfur-containing epoxide of this invention is prepared by reacting a fluorinated mercaptan as aforedescribed with epichlorohydrin according to the scheme:

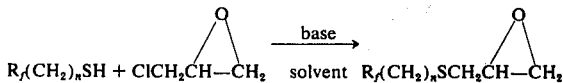

The reaction is advantageously carried out at from about 0°C to 50°C in a suitable solvent such as propanol, 2-propanol, or preferably ethanol, containing in admixture a basic substance such as sodium hydroxide, potassium hydroxide or the like, in sufficient amount to neutralize by-product HCl. The following example is representative of such a preparation.

EXAMPLE 1

To a solution of 4.0g (0.1 mole) of sodium hydroxide in 60 ml. of ethanol is added 53.0 g (0.1 mole) of $(CF_3)_2CF(CF_2)_6C_2H_4SH$ and the mixture stirred for 30 minutes. The solution is added over a 30 minute period to a solution of 93 g (1.0 mole) of epichlorohydrin in 50 ml of ethanol at 25°C. After addition is completed, the reaction mixture is heated to reflux for 3 hours, then cooled and diluted with 500 ml of 1,1,2-trichloro-1,2,2-trifluoroethane. After cooling the reaction mixture is filtered and the solvent stripped from the filtrate to leave 55.5 g of crude liquid product. Vacuum distillation yields 45 g of clear liquid epoxide, b.p., 100°/0.1 mm. Hg., having the formula

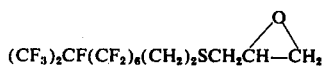

Analysis:
Calc'd for $C_{14}F_{19}H_9OS$: C, 28.67; H, 1.54; F, 61.57; S, 5.46%. Found: C, 28.74; H, 1.64; F, 62.30; S, 5.46%.

The fluoroalkyl sulfur-containing epoxides are useful as adhesion promotors and as leveling agents in fluoropolymer protective coatings formulations as demonstrated by the following example:

EXAMPLE 2

A vinylidene fluoride polymer coating composition is prepared from the following recipe:

| | |
|---|---|
| "KYNAR" microground polyvinylidene fluoride (Pennwalt Corporation) | 600 g |
| Titanium dioxide pigment | 280 g |
| Zinc oxide pigment | 170 g |
| Carbitol acetate | 750 g |
| Dimethyl phthalate | 250 g |
| "Catanac SN" quaternary ammonium salt cationic surfactant | 2 g |

To a 125 g portion of the above formulation is added 0.625 g(0.5%) of the epoxide from Example 1, and the mixture shaken 15 minutes on a paint mixer.

The test formula and a control with no additive are milled in 8 oz. ball-mill jars using 175 g of 0.5 inch Burundum cylinders, and the formulations applied to Al 412 Q-panels using a 0.5 inch, 20 turn-per-inch Meyer bar. The coatings are oven-cured at 450°F for 10 minutes, and finally rated on a scale of 0–10, with the rating of 10 signifying excellent results:

| Property of Coating | Control | With Epoxide Additive |
|---|---|---|
| 45° Knife-cut adhesion | 1 | 9 |
| Flow and leveling | 5 | 7 |
| Pin holes | 0 | 7 |

The results demonstrate that the fluorinated epoxide gives marked and significant improvements to the coating.

PREPARATION OF TWIN-TAILED ALCOHOL.

The twin-tailed fluoroalkyl sulfur-containing alcohol of this invention $[R_f(CH_2)_nSCH_2]_2CHOH$, is readily prepared from the aforedescribed fluoroalkyl epoxide by further reaction with the fluoroalkyl mercaptan (according to Reaction I, below) or by the reaction of two moles of the mercaptan with one mole epichlorohydrin wherein the fluoroalkyl epoxide is a transitory intermediate (Reaction II, below):

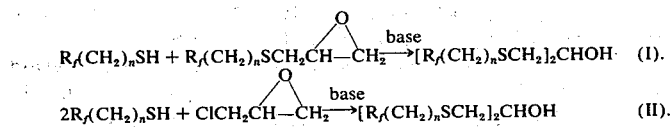

Reaction No. I is advantageously carried out at from about 0°C to 80°C, preferably using a solvent as reaction medium such as ethanol or 2-propanol and a trace of base such as sodium hydroxide or sodium ethoxide. Reaction No. II is conducted at about 0°C to 80°C in a suitable solvent such as ethanol or 2-propanol, containing in admixture a basic material such as sodium hydroxide, potassium hydroxide or the like in sufficient amount to neutralize by-product HCl. The following example is representative of such a preparation.

EXAMPLE 3

A 200 flask fitted with stirrer, condenser, and addition funnel is charged with 20 ml of ethanol and 53.0 g (0.1 mole) of $C_9F_{19}CH_2CH_2SH$. To this is added slowly a solution of 2.0 g (0.05 mole) NaOH in 30 ml of ethanol and the mixture is stirred for 30 minutes. Epichlorohydrin, 4.62 g (0.05 mole), is added dropwise from the addition funnel and heat of reaction is noted. After addition is completed, the mixture is refluxed for 1 hour and then cooled. The mass is taken up in 1,1,2-trichloro-1,2,2-trifluoroethane solvent and filtered to remove salt. Removal of the solvents on the steam bath yields 52.1 g (94%) of white crystalline product, m.p. 78°–80°C., having the structure $(C_9F_{19}CH_2CH_2SCH_2)_2CHOH$.

Analysis:

Calc'd for $C_{25}F_{38}H_{14}OS$: C, 26.89; H, 1.26; F, 64.67; S, 5.74%. Found: C, 26.73; H, 1.37; F, 62.56; S, 6.38%.

The described twin-tailed alcohols of this invention have two highly fluorinated chains in close proximity and can be incorporated into reactive molecules such as resins, polymers, isocyanates, etc. In contrast to the well-known fluorinated alcohols of the art, these alcohols can introduce twice as many fluorinated chains per functional site, that is, for the same number of fluorinated chains introduced, more reactive sites are left free for other useful reactions, such as crosslinking.

PREPARATION OF URETHANE RESINS FROM TWIN-TAILED ALCOHOL.

The twin-tailed alcohol, $[R_f(CH_2)_nSCH_2]_2CHOH$, is a precursor for derivatives particularly useful as oil and water repellents for fibrous substrates, and also useful as surfactants, protective coatings, thickeners, hair spray additives and pressure sensitive adhesives. Such derivatives have the general formula

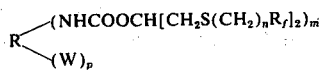

where R is a radical of 2 to 30 carbon atoms free from nonaromatic unsaturation selected from the group consisting of an unsubstituted hydrocarbon radical, an alkoxy substituted or chlorine substituted hydrocarbon radical, and a radical of the structure corresponding to that derived from the reaction of a hydrocarbon isocyanate or an alkoxy substituted or chlorine substituted hydrocarbon isocyanate with the reactive hydrogen of a hydrocarbyl alcohol, hydrocarbyl mercaptan, hydrocarbyl phenol, hydrocarbyl thiophenol, hydrocarbyl carboxylic acid or hydrocarbyl amine; W is —NCO, —NHCONR'R', —NHCOOR' or —NHCOSR' where R' is independently H or an organic group; $m$ is an integer of 1–3; $p$ is an integer of 0–5; and $m + p$ is 2–6.

The urethane resin derivatives of the above formula are particularly valuable in modifying fibrous, porous and continuous surfaces, such as papers, textiles, glass, wood, leather, fur, asbestos, bricks, concrete, metals, ceramics, plastics, painted surfaces, sponges and plaster. The preferred types of articles for modification are papers, textiles and leathers. Especially valuable is the ability of surfaces treated with these adducts to better withstand abrasive action (in addition to the advantages incident to the repellency of oil and water and resistance to soiling imparted by coating with such adducts).

The initial step in preparing the urethane resin is to react the twin-tailed alcohol with an equimolar amount of organic isocyanate, preferably a polyisocyanate and most preferably a diisocyanate. Typical of operable isocyanate reactants are:

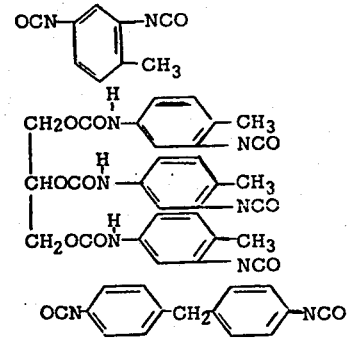

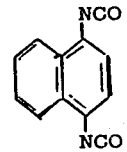

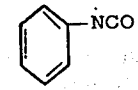

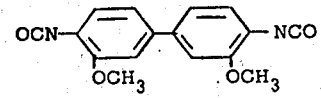

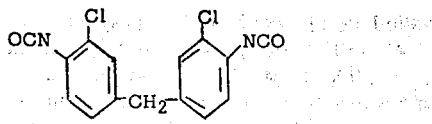

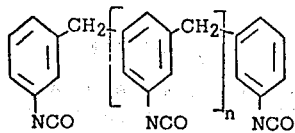

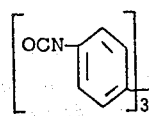

When the isocyanate reactant is a polyisocyanate, the derivative is further reacted with an organic compound having an active hydrogen atom in sufficient amount to react with free isocyanate groups thereon. Representative compounds having active hydrogen suitable for such reaction are exemplified by alcohols, acids, amines, mercaptans and amides, for example:

$CH_3(CH_2)_nOH$     $n = 0–24$
$CH_3CHOHCH_3$
$CH_3(CH_2)_nCOOH$     $n = 0–18$
$(CH_3)_2NH$
$CH_3(CH_2)_nNH_2$     $n = 0–18$
$CH_3(CH_2)_nSH$     $n = 0–18$

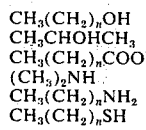

$HOC_2H_4(OC_2H_4)_nOH$     $n = 0–50$

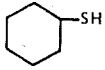

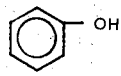

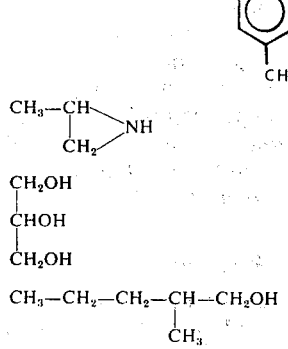

$CH_2OH$
$|$
$CHOH$
$|$
$CH_2OH$ $CH_3—CH_2—CH_2—CH—CH_2OH$
                           $|$
                           $CH_3$

Urethane resins prepared from the twin-tailed fluoroalkyl alcohol embodied in this invention are surprisingly superior in performance to similar resins prepared from alcohols known previously in the art, as is demonstrated by the following Examples 4 – 7, in which the representative polyisocyanate reactant is an aryl diisocyanate.

EXAMPLE 4

To a stirred solution of 5.5 g (0.0315 mole) of 2,4-toluene diisocyanate in 40 ml of $CH_3CCl_3$ at room temperature is added 35.5 g (0.0314 mole) of the fluorinated alcohol product of Example 3, followed by one drop of a stannous type urethane catalyst (e.g., M & T Chemicals "T-9"). The reaction mixture is heated at 25°–44°C for one-half hour and then at 44°–50°C for 2 hours. A solution of 2.96g (0.0315 mole) of phenol in 10 ml of $CH_3CCl_3$ is then added and the reaction mixture heated at 50°–80°C for one hour. The solution is then diluted to 25% solids concentration with $CH_3CCl_3$, and a few drops of methanol to remove traces of unreacted isocyanate from the product resin, for which the following structure is postulated:

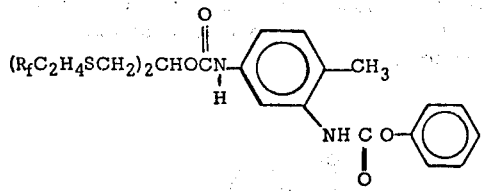

EXAMPLE 4b

The procedure of Example 4a is carried out except that methanol replaces phenol as the active hydrogen-containing reactant to yield a resin, for which the following structure is postulated:

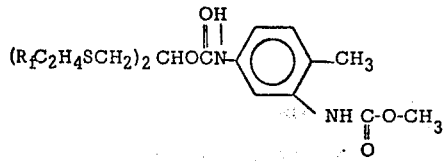

EXAMPLE 4c

Ethyleneimine or methylaziridine (these reactants give essentially equivalent results) replace the phenol of Example 4a to give a resin, for which the following structure is postulated:

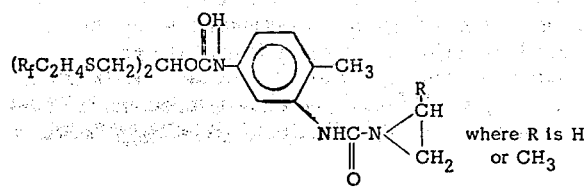

EXAMPLE 4d

The mono-tailed alcohol $(CF_3)_2CF(CF_2)_7CONHC_2H_4OH$ (19.1 g, 0.0315 mole) replaces the twin-tailed alcohol of Example 4a to give a resin, for which the following structure is postulated:

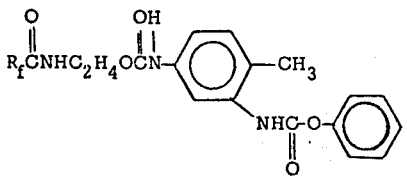

EXAMPLE 4e

The mercaptan of the structure $(CF_3)_2CF(CF_2)_6C_2H_4SH$ (16.7 g, 0.0315 mole) replaces the twin-tailed alcohol of Example 4a to give a resin as follows:

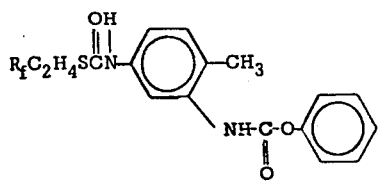

EXAMPLE 4f

The mercaptan of Example 4e replaces the twin-tailed alcohol of Example 4b to give a resin as follows:

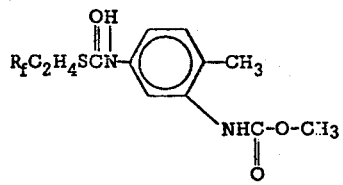

EXAMPLE 5a

The resinous reaction product of (a) the twin-tailed alcohol embodied herein, (b) trimethylolpropane, and (c) 2,4-toluene diisocyanate is prepared as follows:

To a stirred solution of 16.5 g (0.094 mole) of 2,4-toluene diisocyanate, 10 ml. of ethyl acetate, and 1 drop of M & T Chemical's T-9 stannous-type catalyst is added 4.2 g (0.0315 mole) of trimethylolpropane. The mixture is heated to reflux over the next two hours and then 35 g (0.0315 mole) of the twin-tailed alcohol from Example 3, $[(CF_3)_2CF(CF_2)_6C_2H_4SCH_2]_2CHOH$, is added along with 100 ml of ethylacetate. After 3 hours at 40°–50°C, the reaction mixture separates into two layers. The upper layer shows no fluorine by infrared and is discarded. The reaction product (bottom layer), having —NCO functionality, is usable as such, not only for further reactions, but is also useful as a water and oil repellent treatment material for leather.

EXAMPLE 5b

A resinous reaction product is prepared by following the procedure of Example 5a except that the mercaptan $(CF_3)_2CF(CF_2)_6CH_2CH_2SH$ (16.7 g., 0.0315 mole) replaces the twin-tailed alcohol reactant.

EXAMPLE 5c

A resinous reaction product is prepared according to the procedure of Example 5a except that the alcohol $(CF_3)_2CF(CF_2)_7CONHC_2H_4CH$ (20.5 g., 0.0315 mole) replaces the twin-tailed alcohol.

The foregoing products are diluted to 0.8% solids in $CH_3CCl_3$ and sprayed onto sueded pigskin. The following oil and water repellencies are obtained (Spray ratings are according to AATCC Standard Test Method 52-1952 of the American Association of Textile Chemists and Colorists, and oil ratings are by the "3M method" described in U.S. Pat. No. 3,304,378).

| Product of Example | Repellency Ratings | | | |
|---|---|---|---|---|
| | Initial | | After Abrasion | |
| | Oil | Water | Oil | Water |
| 4a | 100+ | 100– | 100 | 80+ |
| 4b | 100+ | 90 | 100 | 90– |
| 4c | 100 | 100 | 100 | 90 |
| 4d | 100 | 80+ | 80 | 80– |
| 4e | 90 | 90+ | 70 | 80+ |
| 4f | 90 | 100 | 60 | 80 |
| 5a | 100+ | 100 | 90 | 90 |
| 5b | 90 | 100 | 50– | 80– |
| 5c | 80 | 100 | 50 | 80 |

Samples were abraded with a fiber brush of the type used to scrub floors, the sample being given 10 heavy rubs — first vertically and then horizontally.

The products prepared from the alcohol of this invention (Examples 4a, 4b, 4c and 5a) are clearly superior, having excellent repellency both initially and after abrasion. Example 4d product is within the scope of U.S. Pat. No. 3,398,182 (Claim 4) describing resins said to have especially good abrasion resistance, and its poor performance emphasizes the unexpected superiority of the resins of this invention.

Urethane resins prepared with the twin-tailed alcohols of the invention also have an important and unexpected consistency of performance under various application conditions likely to be encountered in actual use as shown in the following Examples 6 and 7.

EXAMPLE 6

In three separate preparations, isocyanate-containing products similar to those of Example 5, except made from the fluorinated reactant shown in the table below, are reacted with stoichiometric amounts of 1:1 molar mixtures of ethyleneimine and allyl alcohol at reflux for 3 hours to give resin concentrates containing equimolar amounts of these reactants and the fluorinated reactant. These products are applied to 80 × 80 cotton fabric from a 0.5% solution in $CH_3CCl_3$ containing a small amount of acetone or ethyl acetate to aid solubility, and the fabric dried at three temperatures with the following results (oil repellency is measured by AATCC Standard Test Method 118):

| | Fluorinated Reactant | Oil Repellency Ratings | | |
|---|---|---|---|---|
| | | 25°C | 100°C | 165°C |
| (6a) | $(C_9F_{19}C_2H_4SCH_2)_2CHOH$ | 5 | 6 | 5 |
| (6b) | $C_9F_{19}C_2H_4SC_2H_4OH$* | 5 | 4 | 4 |
| (6c) | $C_9F_{19}C_2H_4SH$ | 5 | — | 2 |

*See Example 17 for Preparation.

Superior results are demonstrated for the product (Example 6a) derived from the twin-tailed alcohol of this invention.

EXAMPLE 7

Resins made by the procedure of Examples 5 and 6 and consisting of the reaction product of trimethylolpropane, 2,4-toluene diisocyanate and the reactants A, B and C designated in the following table, in the molar ratio of 1:3:1:1:1, are prepared and applied to 80 × 80 cotton cloth from 0.5% solution in $CH_3CCl_3$ using two cure temperatures, with the following results:

| | REACTANTS | | Repellency Ratings | | | |
|---|---|---|---|---|---|---|
| | | | 25°C | | 150°C | |
| A | B | C | Oil | Water | Oil | Water |
| Alcohol from Exp 3 | $C_{13}H_{27}OH$ | $\begin{matrix}CH_2\\|\\CH_2\end{matrix}\!\!>\!\!NH$ | 5 | 100 | 5 | 90 |
| Alcohol from Exp 3 | $\begin{matrix}CH_3CH\\|\\CH_2\end{matrix}\!\!>\!\!NH$ | $\begin{matrix}CH_3\!-\!CH\\|\\CH_2\end{matrix}\!\!>\!\!NH$ | 5 | 90+ | 5 | 100 |
| Alcohol from Exp 3 | $\begin{matrix}CH_3CH\\|\\CH_2\end{matrix}\!\!>\!\!NH$ | $C_6H_5CH_2OH$ | 5 | 90+ | 5 | 90+ |
| Alcohol from Exp 3 | $\begin{matrix}CH_3CH\\|\\CH_2\end{matrix}\!\!>\!\!NH$ | $(C_2H_5)_2NH$ | 5 | 90 | 5 | 90+ |
| Alcohol from Exp 3 | $\begin{matrix}CH_3CH\\|\\CH_2\end{matrix}\!\!>\!\!NH$ | $(C_2H_5)_2NOH$ | 5 | 90+ | 5 | 90+ |
| $C_9F_{19}C_2H_4SH$ | $C_9F_{19}C_2H_4SH$ | $\begin{matrix}CH_3\!-\!CH\\|\\CH_2\end{matrix}\!\!>\!\!NH$ | 4 | 90 | 2 | 100 |
| $C_9F_{19}C_2H_4SH$ | $C_{13}H_{27}OH$ | $\begin{matrix}CH_3\!-\!CH\\|\\CH_2\end{matrix}\!\!>\!\!NH$ | 3 | 80 | 1 | 100 |

PREPARATION OF PHOSPHATE DERIVATIVES OF TWIN-TAILED ALCOHOL

Novel phosphate derivatives of the twin-tailed alcohol of this invention which have an average of 1-2 fluorinated alcohol molecules per atom of phosphorus are described by the structure:

$$([R_f(CH_2)_nSCH_2]_2CHO)_xP\!\!\stackrel{\displaystyle O}{\phantom{P}}\!\!Z_{3-x}$$

where $x$ is 1-2 and Z is chosen to give the desired solubility and reactivity properties. For example, Z can be Cl, OH, $-OC_2H_5$, $-OC_2H_4OH$,

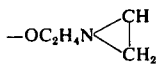

$-^+ONH_4$,

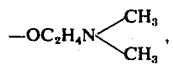

$-NHC_2H_4OH$, or a divalent group such as $-OC_2H_4O-$.

The phosphate derivatives embodied herein are useful in the treatment of paper stock. The preparation and utility of a representative compound is set forth in Example 8.

EXAMPLE 8

A flame dried flask fitted with stirrer, reflux condenser, and nitrogen inlet is charged with 25 ml of dry tetrahydrofuran, (3.06 g, 0.02 mole) of distilled phosphorus oxychloride, and (4.3g, 0.043 mole) of distilled triethylamine. The twin-tailed alcohol product of Example 3 (44.6 g, 0.04 mole) in 100 ml of dry tetrahydrofuran is added dropwise, maintaining the reaction temperature at 20°C. When half the fluorinated alcohol is added, the reaction temperature is raised to reflux. After 3 hours the amber reaction mixture is allowed to cool and the triethylamine hydrochloride filtered off to give a solution of the product

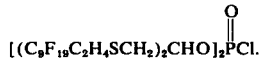

A portion of the filtrate (equivalent to 0.0086 mole) is mixed with 0.9 g (0.009 mole) of distilled triethylamine and 0.20 g (0.013 mole) of distilled water and heated at reflux for 2 hours, cooled, filtered and stripped of solvent to yield 15.2 g (76% yield) of a tan waxy material having an infrared spectrum consistent with the structure:

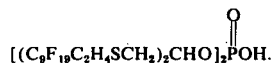

The ethanolamine salt is prepared by dissolving 2.3 g of the acid product obtained above in 50 ml of dry benzene and adding this slowly to 0.1 g of ethanolamine in refluxing benzene. A white precipitate immediately forms which is isolated by filtration after cooling. The solid is soluble in a 1:1 isopropanol/water mixture and, when applied to Kraft paper by padding, gives the excellent performance shown in the following table:

| % Solids in Pad Bath | Kit Rating | Spray |
|---|---|---|
| 0.56 | 10 | 50 |
| 0.28 | 9 | 50 |

The "kit rating" is defined as the highest numbered solution in the table below that will stand on the surface of the paper for 15 seconds in the form of drops without penetration as detected by darkening. Darkening of even a small fraction of the area under the drop is considered a failure.

| Rating Kit No. | Volume Castor Oil | Volume Toluene | Volume Heptane |
|---|---|---|---|
| 1 | 200 | 0 | 0 |
| 2 | 180 | 10 | 10 |
| 3 | 160 | 20 | 20 |
| 4 | 140 | 30 | 30 |
| 5 | 120 | 40 | 40 |
| 6 | 100 | 50 | 50 |
| 7 | 80 | 60 | 60 |
| 8 | 60 | 70 | 70 |
| 9 | 40 | 80 | 80 |
| 10 | 20 | 90 | 90 |
| 11 | 0 | 100 | 100 |
| 12 | 0 | 90 | 110 |

Further examples of useful derivatives prepared from the twin-tailed alcohols of the invention are shown in Examples 9 - 13 below.

PREPARATION OF ACRYLATE ESTER OF TWIN-TAILED ALCOHOL,

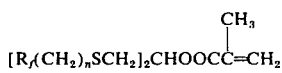

AND POLYMER THEREOF.

EXAMPLE 9

A mixture of 112 g (0.1 mole) of the alcohol from Example 3, 12.1 g (0.12 mole) of triethylamine and 12.5 g (0.12 mole) of methylacrylyl chloride in 250 ml $CH_2Cl_2$ is heated at reflux for one hour. The reaction mixture is filtered and the filtrate washed three times with 1% HCl and three times with water. Removal of the solvent and molecular distillation affords the methacrylate ester in good yield. Polymerization of the monomer in 1,1,2-trichloro-1,2,2,-trifluoroethane using $\alpha, \alpha'$-azobisisobutyronitrile as catalyst gives a solution of polymer that on further dilution provides good oil and water repellent properties to textiles and paper. The acrylic acid ester of the twin-tailed alcohol, and polymer thereof, are also prepared in a like manner. Copolymers of these fluoroalkyl acrylates with other ethylenically unsaturated monomers are similarly prepared.

PREPARATION OF MALEIC ANHYDRIDE RESIN DERIVATIVE OF TWIN-TAILED ALCOHOL.

EXAMPLE 10

A mixture of 50 g (0.4 mole) of ethylene-maleic anhydride resin (Monsanto EVA-21), 45 g (0.04 mole) of the alcohol of Example 3, 200 ml. of xylene and 1 g of p-toluenesulfonic acid is refluxed for 24 hours to yield a partially esterified polymer product. The solvent is removed under vacuum and the product dissolved in aqueous ammonia to give a 1% solution. When this is padded onto 65/35 Dacron polyester-cotton fabric, oil repellency and soil release characteristics are obtained.

PREPARATION OF THE CARBAMATE OF TWIN-TAILED ALCOHOL.

EXAMPLE 11.

A 2-liter flask fitted with a distillation column is charged with 560 g (0.5 mole) of the alcohol from Example 3, 49 g (0.5 mole) of $H_2NCOOC_2H_5$, and 400 ml of toluene. Toluene is distilled until the system is dry and then 5 ml of tetraisopropyl orthotitanate is added. The toluene-ethanol azeotrope is removed as fast as it is formed and the reaction is over in about 5 hours. The toluene is removed by distillation at reduced pressure and the residue poured into pans to solidify and air dry. An excellent yield of the product

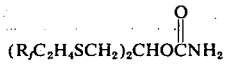

is obtained, m.p. 60°–65°C.

PREPARATION OF SULFUR CONTAINING DIOL

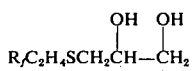

AND DERIVATIVES.

EXAMPLE 12 a

A flask is charged with 58.6 g (0.1 mole) of the epoxide of Example 1, 100 ml of water, 100 ml of ethanol, and 1 ml of concentrated hydrochloric acid, and the mixture boiled for 18 hours. Removal of the solvents by evaporation affords the desired product in good yield.

The material may also be prepared by the method described in Example 2 of the copending application of Toukan and Hauptschein, filed Aug. 12, 1971, Ser. No. 171,325, or also by the following method.

EXAMPLE 12b

A 500 ml reaction flask is charged with 50 g (0.094 mole) of $(CF_3)_2CF(CF_2)_6C_2H_4SH$, 5.1 g (0.094 mole) of sodium methoxide and 100 ml of methanol. To this is slowly added glycidol while maintaining the temperature at 25°C with an ice bath. After addition is completed, the reaction mixture is stirred for 3 hours, and then there is added 150 ml of water and enough concentrated hydrochloric acid to neutralize the base. Extraction with 1,1,2-trichloro-1,2,2-trifluoroethane and evaporation of solvent affords 53 g of $(CF_3)_2CF(CF_2)_6C_2H_4SCH_2CH(OH)CH_2OH$, m.p. 92°–95°.
Analysis:

Calc'd for $C_{14}H_{11}F_{19}O_2S$: C, 27.82; H, 1.83; F, 59.73; S, 5.31.

Found: C, 27.87; H, 1.97; F, 59.77; S, 5.50.

The diols prepared as in Examples 12a and 12b can be used to prepare urethanes (Example 13) useful as oil and water repellents, and can be used in condensation polymerization reactions to give polyesters. Suitable polyacids are, for example, adipic acid, phthalic anhydride, terephthalic acid, pyromellitic acid, maleic acid, fumaric acid, and the fluorine containing diacid disclosed by Hager in U.S. Pat. No. 3,471,518. (Example 14). Carbamates of the diol of Example 12 and especially their methylolated derivatives are useful textile treating agents to achieve oil and water repellency as exemplified in Example 15, as are the acrylate esters of the diol (Examples 16a and b).

PREPARATION OF URETHANE RESIN OF SULFUR-CONTAINING DIOL.

EXAMPLE 13

A dry flask is charged with 25 ml of ethyl acetate, 1.74 g (0.01 mole) of 2,4-toluene diisocyanate, and 3.02 g (0.005 mole) of the diol from Example 12. One drop of tin catalyst (M & T Co's T9 product) is added and the reaction treated at 40° for 1.5 hours. Then 0.48 g (0.005 mole) of phenol is added and the reaction mixture heated 3.5 hours at 50°. Finally, 0.22 g (0.005 mole) of ethyleneimine is added and the product stirred 4 hours at room temperature.

Cotton fabric sprayed with 0.5% solution of this resin in methyl chloroform is highly oil and water repellent.

PREPARATION OF AN ALKYD RESIN OF SULFUR-CONTAINING DIOL.

EXAMPLE 14

A beaker is charged with 35.1 g (0.05 mole of the diol of Example 12, 2.8 g (0.03 mole) of glycerol and 14.8 g (0.1 mole) of phthalic anhydride, and the mixture heated for 2 hours on a hot plate at 275°–300°C. The resulting resin is diluted to 1% in a 1:1 mixture of toluene and butyl acetate and is useful for imparting oil and water repellency to suede leather and textiles.

PREPARATION OF A CARBAMATE OF THE SULFUR-CONTAINING DIOL.

EXAMPLE 15.

A solution of 4.6 g (0.04 mole) of $CF_3COOH$ in 25 ml of benzene is added to a slowly stirred mixture of 12.1 g (0.02 mole) of $R_fCH_2CH_2SCH_2CH(OH)CH_2OH$ (prepared in Example 12) and 2.6 g (0.04 mole) of sodium cyanate in 50 ml of benzene. The mixture is stirred at room temperature for 17 hours. The reaction mixture is filtered from sticky insoluble material, washed with 2 × 50 ml of hot water and dried at 40°–50° under reduced pressure to afford 13.0 g (100% yield) of soft waxy solid, the terminal carbamate with the postulated structure: $(CF_3)_2CF(CF_2)_6CH_2CH_2SCH_2OH(OH)CH_2OCONH_2$.

Infrared spectrum and elemental analysis are in agreement with the above structure.

Analysis:

Calc'd. for $C_{15}H_{12}F_{19}NO_3S$: C, 27.83; H, 1.87; N, 2.16. Found: C, 27.57; H, 1.93; N, 1.74.

When applied to textile either alone or in combination with durable press reactants the fabric is made durably oil and water repellent.

PREPARATION OF ACRYLATES OF THE SULFUR-CONTAINING DIOL.

EXAMPLE 16a

To a stirred ice-cooled solution of 12.1 g (0.02 mole) of $R_fCH_2CH_2SCH(OH)CH_2OH$ from Example 12 and 2.0 g (0.02 mole) of triethylamine in 75 ml of anhyd. ether is added drop by drop a solution of 2.5 g (0.024 mole) of methacrylyl chloride and 0.01 g of p-methoxyphenol in 25 ml of anhyd. ether. The white mixture is refluxed for 2.5 hours. The reaction mixture is filtered to remove a white solid (discarded). The filtrate is washed with 100 ml of water, 100 ml. of 5% NaOH solution and 100 ml of water, dried with anhydrous calcium sulfate, and the solvent then stripped off to afford 11.7 g (87% yield) of light brown viscous liquid residue,

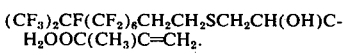

Analysis:

Calc'd for $C_{18}H_{15}F_{19}O_3S$: C, 32.16; H, 2.25; S, 4.77. Found: C, 32.23; H, 2.62; S, 3.83.

EXAMPLE 16b

To a stirred ice-cooled solution of 12.1 g (0.02 mole) of $R_fCH_2CH_2SCH(OH)CH_2OH$ from Example 12 and 6.1 g (0.06 mole) of triethylamine in 75 ml of 1,1,2-trichloro-1,2,2-trifluoroethane is added drop by drop a solution of 6.3 g (0.06 mole) of methacrylyl chloride and 0.02 g of p-methoxyphenol in 25 ml of 1,1,2-trichloro-1,2,2-trifluoroethane. The white mixture is refluxed for 4.5 hours. The reaction mixture is filtered to separate a white solid (discarded). The filtrate is washed with 100 ml of water, 100 ml of 5% NaOH solution and 100 ml of water, dried with anhydrous calcium sulfate, and the solvent then stripped off to afford 14.5 g (100% yield) of light brown viscous liquid residue.

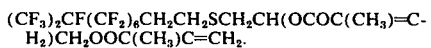

Solution polymerization of the monomers of Example 16a & b in 1,1,2-trichloro-1,2,2-trifluoroethane using α, α'-azobisisobutyronitile catalyst at 70°C for 8 hours give solutions that impart good oil and water repellency to leather and textiles.

Thus, as the foregoing demonstrates, sulfur-containing diols and derivatives are provided by this invention represented by the formula

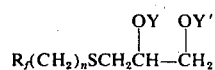

where $R_f$ and $n$ are as previously defined and Y and Y' are independently selected from the group consisting of

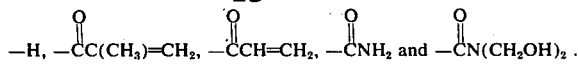

Yet further useful derivatives of the fluorinated mercaptans are the reaction productions of amines with the new epoxide being obtained according to the reaction:

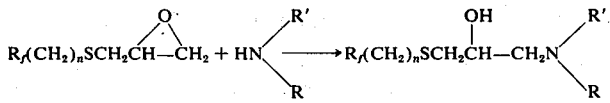

where $R_f$ and n are as previously defined and R and R' are independently H, alkyl, substituted alkyl, or may be part of a polymeric system. Typical specific compounds of the class are:

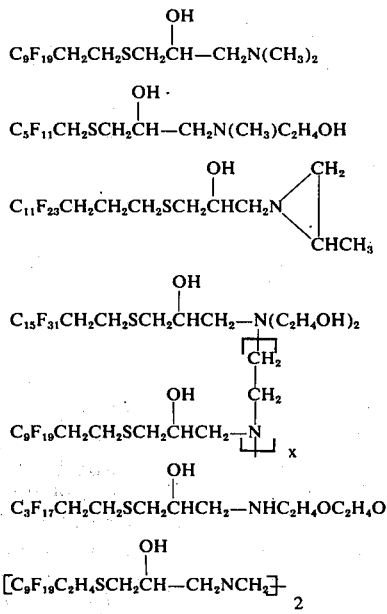

These compounds are readily made by merely gently heating an equivalent amount of the epoxide and amine together, with or without a solvent. For example, the second compound is obtained by warming 58.6 g (0.1 mole) of the epoxide of Example 1 with 7.2 g (0.1 mole) of $CH_3NHC_2H_4OH$ at 40°C for 4 hours. In like manner, the others are obtained from readily available amines including the polymeric ethyleneimine. The compounds are extremely versatile intermediates. They can be converted to ammonium salts for use as surfactants. They can be reacted with ethylene or propylene oxide to provide nonionic surfactants, and, of course, these condensates can be made into ammonium salts. Because of the reactive hydroxyl it is possible to prepare useful acrylate monomers, urethane resins, and carbamates. Because these systems can be made cationic, they have particular utility where substantivity is desirable such as in home treatment of garments to render them oil and water repellent.

PREPARATION OF $R_f C_2H_4SC_2H_4OH$ AND DERIVATIVES.

EXAMPLE 17

This compound is cited as a less preferred alcohol reactant in Example 6.

A 500 ml flask is charged with 100 ml of methanol, 5.4 g (0.1 mole) of sodium methoxide, and 53 g (0.1 mole) of $(CF_3)_2CF(CF_2)_6C_2H_4SH$ and the mixture stirred for 30 minutes at 5°C. To this is added 4.6 g (0.105 mole) of liquid ethylene oxide keeping the temperature below 5°. After stirring for 1 hour, 100 ml of water is added and the product acidified to litmus with conc. hydrochloric acid. Extraction with 1,1,2-trichloro-1,2,2-trifluoroethane and solvent evaporation affords 41 g of $(CF_3)_2CF(CF_2)_6C_2H_4SC_2H_4OH$, m.p., 69°–71°.

Calc'd for $C_{13}H_9F_{19}OS$; C, 27.18; H, 1.57;F, 62.86;S, 5.58. Found: C, 26.84; H, 1.77;F, 63.18; S, 5.91.

The methacrylate ester is prepared as follows: A 500 ml flask is charged with 50 g (0.087 mole) of the above alcohol product, 11.3 g (0.131 mole) of methacrylic acid, 0.876 g of p-toluene-sulfonic acid, 0.45 g of N, N'-diphenyl-p-phenylene diamine, and 230 ml of xylene, and the mixture refluxed for 8½ hours removing water in a phase splitter. Fractionation under vacuum gives 30 g of liquid monomer $(CF_3)_2CF(CF_2)_6C_2H_4SC_2H_4OOCC(CH_3)=CH_2$, b.p. 114°/0.13 mm.

Calc'd for $C_{17}H_{13}F_{19}O_2S$: C, 31.78; H, 2.03; F, 56.20; S, 4.99.

Found: C, 31,35;H, 2,16;F, 55.89; S, 5.12.

Solution polymerization of this monomer in 1,1,2-trichloro-1,2,2-trifluoroethane using $\alpha, \alpha'$-azi-obisisobutyonitrile catalyst at 70°C for 8 hours gives a solution useful for making fabrics oil and water repellent.

The foregoing adducts and resins of this invention may be applied as a surface treatment by known methods of coating, such as spraying, roll coating, brushing, or dipping from an organic solvent solution or anionic, cationic or nonionic emulsion, or even applied as powders or adherent dusts. They may be applied from readily available organic solvents such as alcohols, ketones, ethers and chlorinated solvents. They may be used as the sole component in the treating liquid or as a component in a complex multi-ingredient formulation, such as cosmetic articles, waxes, polishes, cleaning mixtures and treating agents. For instance, excellent water and oil repellency and soil resistance are obtained on textile fabrics which are treated simultaneously with the adducts of this invention and conventional finishes, such as mildew preventatives, moth resisting agents, crease-proofing resins, lubricants, softeners, sizes, flame retardants, antistatic agents, dye fixatives, and water repellents. In the treatment of paper the adducts may be present as an ingredient in a wax, starch, casein, elastomer, or wet strength resin formulation. Aqueous emulsions of the fluorocarbon compositions are especially useful in the treatment of paper. By mixing the adduct in an aqueous or oil type paint formulation, it may be applied effectively to unpainted asbestos siding, wood, metal and masonry. In the treatment of floors and tile surfaces and like substrates the adducts may be applied by their incorporation in an emulsion or solution.

We claim:

1. A composition of matter having the following formula:

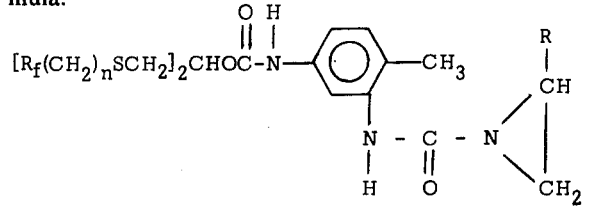

wherein $R_f$ is selected from the group consisting of $CF_3(CF_2)_y$, $(CF_3)_2CF(CF_2)_y$, and $(CF_3)_2CFO(CF_2)_y$ where $y$ is an integer of 1 to 14; $n$ is an integer of 1 to 12, and R is hydrogen or methyl.

2. The composition of matter of claim 1 wherein R is hydrogen.

3. The composition of matter of claim 1 wherein R is methyl.

4. The composition of matter of claim 1 wherein $n$ is 2.

5. The composition of matter of claim 1 wherein $R_f$ is $C_9F_{19}$ and $n$ is 2.

* * * * *